United States Patent [19]

Tomioka et al.

[11] Patent Number: 5,587,492

[45] Date of Patent: Dec. 24, 1996

[54] POLYHYDRIC PHENOL COMPOUND AND POSITIVE RESIST COMPOSITION COMPRISING THE SAME

[75] Inventors: Jun Tomioka, Hyogo; Yasunori Uetani, Osaka; Hirotoshi Nakanishi, Osaka; Ryotaro Hanawa, Osaka; Ayako Ida, Hyogo, all of Japan

[73] Assignee: Sumitomo Chemical Company, Limited, Osaka, Japan

[21] Appl. No.: 423,760

[22] Filed: Apr. 18, 1995

Related U.S. Application Data

[62] Division of Ser. No. 853,547, Mar. 18, 1992, Pat. No. 5,436,107.

[30] Foreign Application Priority Data

Mar. 25, 1991 [JP] Japan ................................ 3-60024

[51] Int. Cl.$^6$ ................................................ C07D 311/60
[52] U.S. Cl. ......................................................... 549/406
[58] Field of Search ..................................... 549/406

[56] References Cited

U.S. PATENT DOCUMENTS 5,059,507  10/1991  Uetani et al. ............................ 430/193

FOREIGN PATENT DOCUMENTS 0346808  12/1989  European Pat. Off. .
0363978   4/1990  European Pat. Off. .

*Primary Examiner*—Nicky Chan
*Attorney, Agent, or Firm*—Birch, Stewart, Kolasch & Birch, LLP

[57] ABSTRACT

A polyhydric phenol compound of the formula:

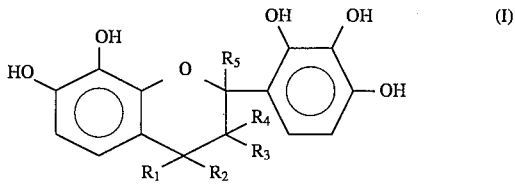

wherein $R_1$ to $R_5$ are independently a hydrogen atom, an alkyl group, an alkenyl group, a cycloalkyl group or an aryl group, provided that at least one of $R_1$ and $R_2$ is an alkyl group, an alkenyl group, a cycloalkyl group or an aryl group, and its quinone diazide sulfonate which gives a positive resist composition having improved sensitivity and a good depth of focus.

3 Claims, No Drawings

POLYHYDRIC PHENOL COMPOUND AND POSITIVE RESIST COMPOSITION COMPRISING THE SAME

This application is a divisional of application Ser. No. 07/853,547, filed on Mar. 18, 1992, now U.S. Pat. No. 5,436,107.

BACKGROUND OF THE INVENTION

1. Field of the Invention

The present invention relates to a polyhydric phenol compound and a positive resist composition which comprises the same and has high sensitivity and a large depth of focus.

2. Description of the Related Art

A composition containing a compound having a quinone diazide group and an alkali-soluble resin finds use as a positive resist, because upon exposure to light having a wavelength of 300 to 500 nm, the quinone diazide group decomposes to form a carboxyl group whereby the originally alkali-insoluble composition becomes alkali-soluble. The positive resist composition has much better resolution than a negative resist composition and is used in the production of integrated circuits such as IC or LSI.

Recently, particularly with integrated circuits, miniaturization has proceeded with a rise in the integration level, which results in demands for formation of patterns of submicron order. To satisfy such demands, a step-and-repeat type reduction projection exposure apparatus, namely a stepper is used as an exposure apparatus.

When a numerical aperture (NA) of a reduction projection lens of the stepper is increased, a resolution is increased but a depth of focus is decreased. Because of the step-and-repeat type, a throughput of the stepper is smaller than that with a batch exposure system. Therefore, the resist composition is required to have a much larger depth of focus and better sensitivity.

However, a resist composition comprising a conventional quinone diazide compound and a conventional alkali-soluble resin has a limit in improvement of the depth of focus and the sensitivity.

For example, if an amount of the quinone diazide compound is increased to increase the depth of focus, serious problems such as deterioration of sensitivity and increase of residues after developing arise.

SUMMARY OF THE INVENTION

One object of the present invention is to provide a novel polyhydric phenol compound and its quinone diazide sulfonate which gives a positive resist composition with improved properties.

Another object of the present invention is to provide a positive resist composition which has a larger depth of focus and good sensitivity with maintaining other properties such as a resolution, heat resistance and the like.

According to a first aspect of the present invention, there is provided a polyhydric phenol compound of the formula:

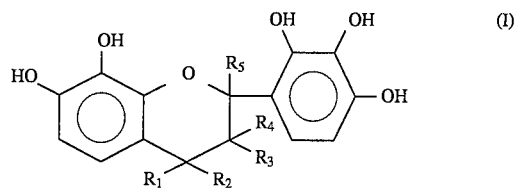

wherein $R_1$ to $R_5$ are independently a hydrogen atom, an alkyl group, an alkenyl group, a cycloalkyl group or an aryl group, provided that at least one of $R_1$ and $R_2$ is an alkyl group, an alkenyl group, a cycloalkyl group or an aryl group, and its quinone diazide sulfonate.

According to the second aspect of the present invention, there is provided a positive resist composition which comprises, in admixture, an alkali-soluble resin and at least one quinone diazide sulfonate of the polyhydric phenol compound of the formula (I).

DETAILED DESCRIPTION OF THE INVENTION

Herein, preferably, the alkyl group has 1 to 4 carbon atoms, the alkenyl group has 2 to 4 carbon atoms, the cycloalkyl group has 3 to 6 carbon atoms, and the aryl group has 6 to 12 carbon atoms.

In the formula (I), $R_1$, $R_2$ or $R_5$ is preferably a $C_1$–$C_4$ alkyl group, in particular a methyl group or an ethyl group. $R_3$ or $R_4$ is preferably a hydrogen atom or a $C_1$–$C_4$ alkyl group, in particular a methyl group or an ethyl group.

Preferred examples of the phenol compound (I) are the following compounds:

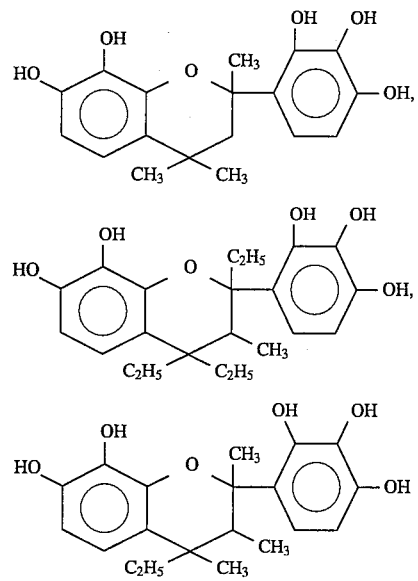

The phenol compound of the formula (I) may be synthesized through a condensation reaction of pyrogallol with a ketone compound in the presence of an acid catalyst such as hydrochloric acid, sulfuric acid, phosphoric acid, p-toluenesulfonic acid, an ion exchange resin having —$SO_3H$ groups and the like. Examples of the ketone compound are acetone, methyl ethyl ketone, methyl isobutyl ketone, methyl cyclohexyl ketone, acetophenone, and the like.

The positive resist composition of the present invention may further contain a quinone diazide sulfonate of a phenol compound of the formula:

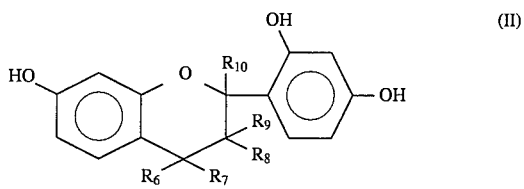

wherein $R_6$ to $R_{10}$ are independently a hydrogen atom, an alkyl group, an alkenyl group, a cycloalkyl group or an aryl group, provided that at least one of $R_6$ and $R_7$ is an alkyl group, an alkenyl group, a cycloalkyl group or an aryl group.

In the formula (II), $R_6$, $R_7$ or $R_{10}$ is preferably a $C_1$-$C_4$ alkyl group, in particular a methyl group or an ethyl group. $R_8$ or $R_9$ is preferably a hydrogen atom or a $C_1$-$C_4$ alkyl group, in particular a methyl group or an ethyl group.

Preferred examples of the compound (II) are the following compounds:

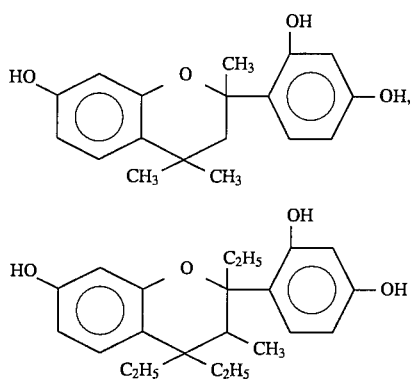

The phenol compound of the formula (II) may be synthesized through a condensation reaction of resorcinol with a ketone compound in the presence of an acid catalyst such as hydrochloric acid, sulfuric acid, phosphoric acid, p-toluenesulfonic acid, an ion exchange resin having —$SO_3H$ groups and the like. Examples of the ketone compound are acetone, methyl ethyl ketone, methyl isobutyl ketone, methyl cyclohexyl ketone, acetophenone, and the like.

The quinone diazide sulfonate of the phenol compound may be prepared by a per se conventional method. For example, the ester is prepared by a condensation reaction of the phenol compound with naphthoquinone diazide sulfonyl halide or benzoquionone diazide sulfonyl halide in the presence of a weak alkali such as sodium carbonate.

Preferably, an esterification rate of the phenol compound (I) is at least 60% and that of the phenol (II) compound is also at least 60%.

A weight ratio of the quinone diazide sulfonate of the phenol compound (I) to the quinone diazide sulfonate of the phenol compound (It) is from 1:3 to 4:1, preferably from 1:2 to 3:1.

The quinone diazide sulfonates of the phenol compound (I) or (II) may be used alone or in combination.

A novolak resin is preferably used as the alkali soluble resin. The novolak resin is prepared by an addition condensation reaction of a phenol with formaldehyde. Specific examples of the phenol used as one of the raw materials for the novolak resin include phenol, cresol, xylenol, ethylphenol, trimethylphenol, propylphenol, butylphenol, dihydroxybenzene, naphthols, etc. These phenols may be used alone or in combination.

The formaldehyde which undergoes the addition condensation reaction with the phenol can be used in the form of an aqueous solution of formaldehyde (formalin) or paraformaldehyde. In particular, 37% formalin which is commercially mass produced is suitably used.

The addition condensation reaction of the phenol with formaldehyde can be carried out according to a usual method. This reaction is carried out at a temperature of 60° to 120° C. for 2 to 30 hours. Organic acids, inorganic acids or divalent metal salts are used as catalysts. Specific examples of the catalyst are oxalic acid, sulfuric acid, hydrochloric acid, perchloric acid, p-toluenesulfonic acid, trichloroacetic acid, phosphoric acid, formic acid, zinc acetate, magnesium acetate, etc.

The reaction may be carried out in the presence or absence of a solvent.

The amount of the quinone diazide sulfonate to be added to the resist composition is from 15 to 50% by weight and that of the alkali-soluble resin is at least 50% by weight, based on the total weight of the solid components in the resist composition.

The positive resist composition is prepared by mixing and dissolving the quinone diazide sulfonate and the alkali-soluble resin in a solvent. Preferably, the used solvent evaporates at a suitable drying rate to give a uniform and smooth coating film. Such solvent includes ethylcellosolve acetate, methylcellosolve acetate, ethylcellosolve, methylcellosolve, propylene glycol monomethyl ether acetate, butyl acetate, methyl isobutyl ketone, xylene and the like. An amount of the solvent is, for example, from 50 to 80% by weight in case of ethylcellosolve acetate.

To the positive resist composition obtained by the foregoing method, small amounts of resins, dyes and the like may be added if desired.

PREFERRED EMBODIMENTS OF THE INVENTION

The present invention will be illustrated more in detail by the following Examples, but it is not limited to these Examples. In Examples, "parts" are by weight.

EXAMPLE 1

To methanol (280 g), pyrogallol (257.3 g) and 36% hydrochloric acid (92.3 g) were added and a mixture was heated up to 45° to 50° C. while stirring to form a homogeneous solution. To the solution, acetone (34.8 g) was dropwise added over 30 minutes, followed by stirring for 8 hours. After the completion of the reaction, to the reaction mixture, water (4 liters) and ethyl acetate (1.1 liters) were added and separated. To an organic layer, water (3 liters), ethyl acetate (200 ml) and toluene (150 ml) were added and a mixture was washed with water. Thereafter, the mixture was washed with water (each 3 liters) three times. The organic layer was concentrated to obtain an oily product (103 g). To the oily material, ethyl acetate (13 g) and toluene (170 g) were added to recrystallize the product. The crystalline product was then dried at 70° C. to obtain the dried product (22.6 g). From following results of $^1$H-NMR, mass spectrum (MS) and the melting point, the product was identified as the compound of the formula:

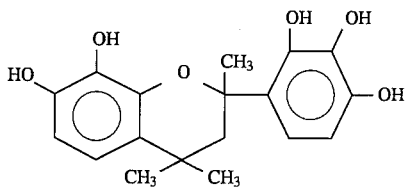

$^1$H-NMR (acetone-d$_6$, TMS): δ (ppm)=0.80 (s, 3H), 1.23 (s, 3H), 1.69 (s, 3H), 1.90 (d, 1H, J=about 14 Hz), 3.01 (d, 1H, J=about 14 Hz), 6.23 (d, 1H, J=8.6 Hz), 6.42 (d, 1H, J=8.6 Hz), 6.50 (d, 1H, 8.6 Hz), 6.57 (d, 1H, J=8.6 Hz), about 7.5 (s, 5H).

MS: m/e=332 (M$^+$).

Melting point: 183°–184° C.

REFERENCE EXAMPLE 1

In a 300 ml three-necked flask, the compound prepared in Example 1 (6.64 g), naphthoquinone-(1,2)-diazide-(2)-5-sulfonyl chloride (24.18 g) (a molar ratio of the compound of Example 1 to naphthoquinone-(1,2)-diazide-(2)-5-sulfonyl chloride was 1:4.5; an esterification rate: 90%. Hereinafter, a molar ratio is that of a phenol compound to a quinone diazide compound) and dioxane (150 g) were charged and stirred to completely dissolve the compounds. Then, the flask was dipped in a water bath to control a reaction temperature at 20° to 25° C., and triethylamine (10.0 g) was dropwise added over 30 minutes while stirring. Thereafter, the reaction mixture was further stirred at 20° to 25° C. for 20 hours. After the completion of the reaction, the reaction mixture was poured in ion-exchanged water, filtered and then dried to obtain a radiation sensitizer B.

REFERENCE EXAMPLE 2

In the same manner as in Reference Example 1 but using the compound prepared in Example 1 in a molar ratio of 1:5 (an esterification rate of 100%), a reaction was carried out to obtain a radiation sensitizer C.

REFERENCE EXAMPLE 3

In the same manner as in Reference Example 1 but using the compound of the formula:

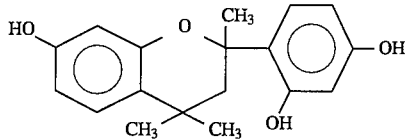

which was prepared according to Example 1 of Japanese Patent Kokai Publication No. 139375/1980 in place of the compound prepared in Example 1 in a molar ratio of 1:2 (an esterification rate of 66.7%), a reaction was carried out to obtain a radiation sensitizer D.

REFERENCE EXAMPLES 4 AND 5

In the same manner as in Reference Example 1 but using 2,3,4,4'-tetrahydroxybenzophenone or 2,3,4,2',4'-pentahydroxybenzophenone in place of the compound prepared in Example 1 in a molar ratio of 1:4 or 1:5 (both an esterification ratio of 100%), a reaction was carried out to obtain a radiation sensitizer E or F, respectively.

EXAMPLES 2 AND 3 AND COMPARATIVE EXAMPLES 1 AND 2

Each of the radiation sensitizers prepared in Reference Examples 1 to 5 and the novolak resin A in amounts shown in the Table were dissolved in ethylcellosolve acetate (48 parts) to prepare a resist solution, which was filtered through a TEFLON (a trademark) filter of 0.2 μm in pore size. The resist solution was coated on a silicone wafer, which had been rinsed in a usual way, by means of a spinner so as to form a resist film of 1.3 μm in thickness. Subsequently, the silicon wafer was baked for 60 seconds on a hot plate kept at 100° C., and exposed to light having a wavelength of 436 nm (g line) while varying the exposure time stepwise by means of a reduction projection exposing apparatus (NSR-1505 G3C with NA of 0.42 manufactured by Nicon). Thereafter, the silicon wafer was post baked (post exposure baking, PEB) on a hot plate kept at 110° C. for 60 second and developed for one minute in a developing solution (SOPD manufactured by Sumitomo Chemical Co., Ltd.) to obtain a positive pattern.

Then, a cross section of a line-and-space pattern of 0.6 μm was observed by a scanning electron microscope (SEM). An exposure time (msec.) at L/S=1 with the best focus was defined as an effective sensitivity, and a degree of focus shifting at which the above line-and-space pattern could be resolved without film thickness decrease was defined as a depth of focus.

The results are shown in the Table.

TABLE

| Exam- | Composition | | Effective | Depth of |
|---|---|---|---|---|
| ple No. | Novolak*$^{1)}$ resin A | Radiation sensitizer | sensitivity (msec.) | focus (μm) |
| 2 | 15 parts | B: 4 parts | 425 | 1.75 |
| 3 | 15 parts | C: 2 parts D: 2 parts | 450 | 2.25 |
| Comp. 1 | 15 parts | E: 4 parts | 600 | 1.25 |
| Comp. 2 | 15 parts | F: 4 parts | 550 | 1.25 |

Note: *$^{1)}$Novolak resin A: A cresol mixture (a molar ratio of m-isomer to p-isomer = 4:6) was reacted with formalin (a molar ratio of the cresols to formalin = 1:0.8) using oxalic acid as a catalyst under reflux to obtain a novolak resin having a weight average molecular weight of 5500 (calculated as polystyrene).

The positive resist composition of the present invention has the excellent properties such as a large depth of focus and a high sensitivity, and the decreased residues after developing.

What is claimed is:

1. A polyhydric phenol compound of the formula:

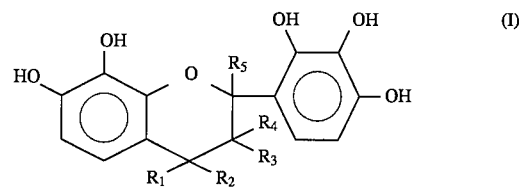

wherein R$_1$ to R$_5$ are independently a hydrogen atom, an alkyl group, an alkenyl group, a cycloalkyl group or an aryl group, provided that at least one of R$_1$ and R$_2$ is an alkyl group, an alkenyl group, a cycloalkyl group or an aryl group.

2. The polyhydric phenol compound according to claim 1, wherein R$_1$, R$_2$ or R$_5$ is a C$_1$–C$_4$ alkyl group, and R$_3$ or R$_4$ is a hydrogen atom or a C$_1$–C$_4$ alkyl group.

3. The polyhydric phenol compound according to claim 2, wherein said alkyl group is a methyl group or an ethyl group.

* * * * *